United States Patent
Kim et al.

(10) Patent No.: US 10,613,172 B2
(45) Date of Patent: Apr. 7, 2020

(54) READOUT ELECTRONICS ARCHITECTURE WITH IMPROVED TIMING RESOLUTION

(71) Applicant: General Electric Company, Schenectady, NY (US)

(72) Inventors: Changlyong Kim, Brookfield, WI (US); Albert Taesung Byun, Guilderland, NY (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 205 days.

(21) Appl. No.: 15/630,334

(22) Filed: Jun. 22, 2017

(65) Prior Publication Data
US 2018/0372822 A1    Dec. 27, 2018

(51) Int. Cl.
*G01R 33/48*  (2006.01)
*G01T 1/164*  (2006.01)
(Continued)

(52) U.S. Cl.
CPC .......... *G01R 33/481* (2013.01); *G01T 1/1603* (2013.01); *G01T 1/1647* (2013.01);
(Continued)

(58) Field of Classification Search
CPC ... G01R 33/481; G01T 1/2985; G01T 1/2018; G01T 1/208; G01T 1/2914; G01T 1/20;
(Continued)

(56) References Cited

U.S. PATENT DOCUMENTS

| | | | | |
|---|---|---|---|---|
| 4,088,962 | A | * | 5/1978 | Trilling ............... H03F 3/45085 330/103 |
| 2008/0103391 | A1 | * | 5/2008 | Dos Santos Varela ..................... G01T 1/1615 600/436 |

(Continued)

FOREIGN PATENT DOCUMENTS

| | | | |
|---|---|---|---|
| CN | 86107132 A | * | 5/1988 |
| JP | 01190085 A | * | 7/1989 |

OTHER PUBLICATIONS

Cova, S., et al.; "Avalanche Photodiodes and Quenching Circuits for Single-Photon Detection", Applied Optics, vol. 35, No. 12, Apr. 20, 1996, pp. 1956-1976.

(Continued)

*Primary Examiner* — Que Tan Le
*Assistant Examiner* — Jennifer D Bennett
(74) *Attorney, Agent, or Firm* — Fletcher Yoder, P.C.

(57) ABSTRACT

A multichannel ASIC for interfacing with an array of photodetectors in a PET imaging system includes a front-end circuit configured to be coupled to the array of photodetectors and to receive analog signals therefrom. The ASIC includes a time discriminating circuit including a low input impedance amplifier configured to be coupled to the array of photodetectors and to receive a signal summing the analog signals from the array of photodetectors and to generate a hit signal for timing pickoff based on the signal. The ASIC includes an energy circuit operably coupled to the front-end circuit and configured to generate a summed energy output signal based on each of the analog signals and summed positional output signal based on each of the analog signals.

18 Claims, 10 Drawing Sheets

(51) Int. Cl.
*G01T 1/29* (2006.01)
*G01T 1/16* (2006.01)
*H01J 40/14* (2006.01)
*A61B 6/03* (2006.01)

(52) U.S. Cl.
CPC ............ *G01T 1/2985* (2013.01); *H01J 40/14* (2013.01); *A61B 6/037* (2013.01)

(58) Field of Classification Search
CPC .. G01T 1/24; G01T 1/247; G01T 1/29; G01T 1/248; G01T 1/00; G01T 1/1647; G01T 1/1603; G01J 1/44; A61B 6/037; H01J 40/14
See application file for complete search history.

(56) References Cited

U.S. PATENT DOCUMENTS

| | | | |
|---|---|---|---|
| 2013/0099100 A1* | 4/2013 | Pavlov | H01L 31/107 250/208.2 |
| 2013/0306876 A1* | 11/2013 | Uchida | G01T 1/1644 250/366 |
| 2014/0224963 A1 | 8/2014 | Guo et al. | |
| 2015/0285922 A1 | 10/2015 | Mintzer et al. | |
| 2016/0084703 A1* | 3/2016 | Shaber | G01T 1/2018 |
| 2016/0170045 A1* | 6/2016 | Kim | G01T 1/2985 250/208.1 |

OTHER PUBLICATIONS

Corsi, F., et al.; "Electrical Characterization of Silicon Photo-Multiplier Detectors for Optimal Front-End Design", 2006 IEEE Nuclear Science Symposium Conference Record, N30-222, pp. 1276-1280.

Corsi, F., et al.; "Modelling a Silicon Photomultiplier (SiPM) as a Signal Source for Optimum Front-End Design", ScienceDirect, Nuclear Instruments and Methods in Physics Research A 572, 2007, pp. 416-418.

Seifert, Stefan, et al.; "Monolithic LaBr3: Ce Crystals on Silicon Photomultiplier Arrays for Time-of-Flight Positron Emission Tomography", Phys. Med. Biol. 57 (2012) pp. 2219-2233.

* cited by examiner

READOUT ELECTRONICS ARCHITECTURE WITH IMPROVED TIMING RESOLUTION

BACKGROUND

The subject matter disclosed herein relates to imaging and, more particularly, to apparatus and methods for processing analog signals generated by solid state photomultiplier devices.

A silicon photomultiplier (SiPM) is an array of passively quenched Geiger-mode avalanche photodiodes (APD) for detecting impinging photons. SiPM can provide information about certain parameters, such as the time of the impingement event, the energy associated with the event, and the position of the event within the detector. These parameters can be determined through processing algorithms applied to the analog signals generated by the SiPM. Some conventional SiPMs can produce very fast signals, which provides a high degree of timing accuracy.

SiPMs provide certain advantages over conventional vacuum photomultiplier tubes (PMTs), and are therefore being used in many applications, including positron emission tomography (PET) for medical imaging. These advantages include better photon detection efficiency (i.e., a high probability of detecting an impinging photon), compactness, ruggedness, low operational voltage, insensitivity to magnetic fields and low cost. However, due to its small size of 2 mm×2 mm to 6 mm×6 mm, compared to a PMT in the dimension of 38 mm×38 mm, multiple SiPMs are required to cover the area of the PMT, which demands an increased amount of readout electronics. In order to take advantage of the improvement in SiPMs without a large cost in both cost and power consumption in the readout electronics, there is a need to simplify the readout architecture coupled to the SiPMs while keeping the integrity of SiPM signals in both rising edge and signal length.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with a first embodiment, a multichannel application specific integrated circuit (ASIC) for interfacing with an array of photodetectors in a positron emission tomography (PET) imaging system is provided. The ASIC includes a front-end circuit configured to be coupled to the array of photodetectors and to receive analog signals therefrom. The ASIC also includes a time discriminating circuit including a low input impedance amplifier configured to be coupled to the array of photodetectors and to receive a signal summing the analog signals from the array of photodetectors and to generate a hit signal for timing pickoff based on the signal. The ASIC further includes an energy circuit operably coupled to the front-end circuit and configured to generate a summed energy output signal and a summed positional output signal based on each of the analog signals, the summed energy output signal representing an energy level of the detected radiation in the array of photodetectors, and the summed positional output signal representing a location of the detected radiation in the array of photodetectors.

In accordance with a second embodiment, a method of interfacing with an array of photodetectors in a positron emission tomography (PET) imaging system is provided. The method includes receiving analog signals from each photodetector in the array of photodetectors using a front-end circuit. The method also includes generating a hit signal for timing pickoff based on a signal summing the analog signals from the array of photodetectors using a time discriminating unit including a low input impedance amplifier. The method further includes generating a summed energy output signal based on each of the analog signals using an energy circuit operably coupled to the front-end circuit, the summed energy output signal representing an energy level of the detected radiation in the array of photodetectors. The method even further includes generating a summed positional output signal based on each of the analog signals using the energy circuit, the summed positional output signal representing a location of the detected radiation in the array of photodetectors.

In accordance with a third embodiment, a multichannel application specific integrated circuit (ASIC) for interfacing with an array of photodetectors in a positron emission tomography (PET) imaging system is provided. The ASIC includes a front-end circuit configured to be capacitive coupled to each photodetector of the array of photodetectors and to receive analog signals therefrom. The ASIC also includes a time discriminating circuit including a low input impedance amplifier configured to be conductive coupled to each photodetector of the array of photodetectors and to receive a signal summing the analog signals from the array of photodetectors and to generate a hit signal for timing pickoff based on the signal, wherein the low input impedance amplifier has an input impedance of 1 Ohm or less. The ASIC further includes an energy circuit operably coupled to the front-end circuit and configured to generate a summed energy output signal based on each of the analog signals and a summed positional output signal based on each of the analog signals, the summed energy output signal representing an energy level of the detected radiation in the array of photodetectors, and the summed positional output signal representing a location of the detected radiation in the array of photodetectors.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
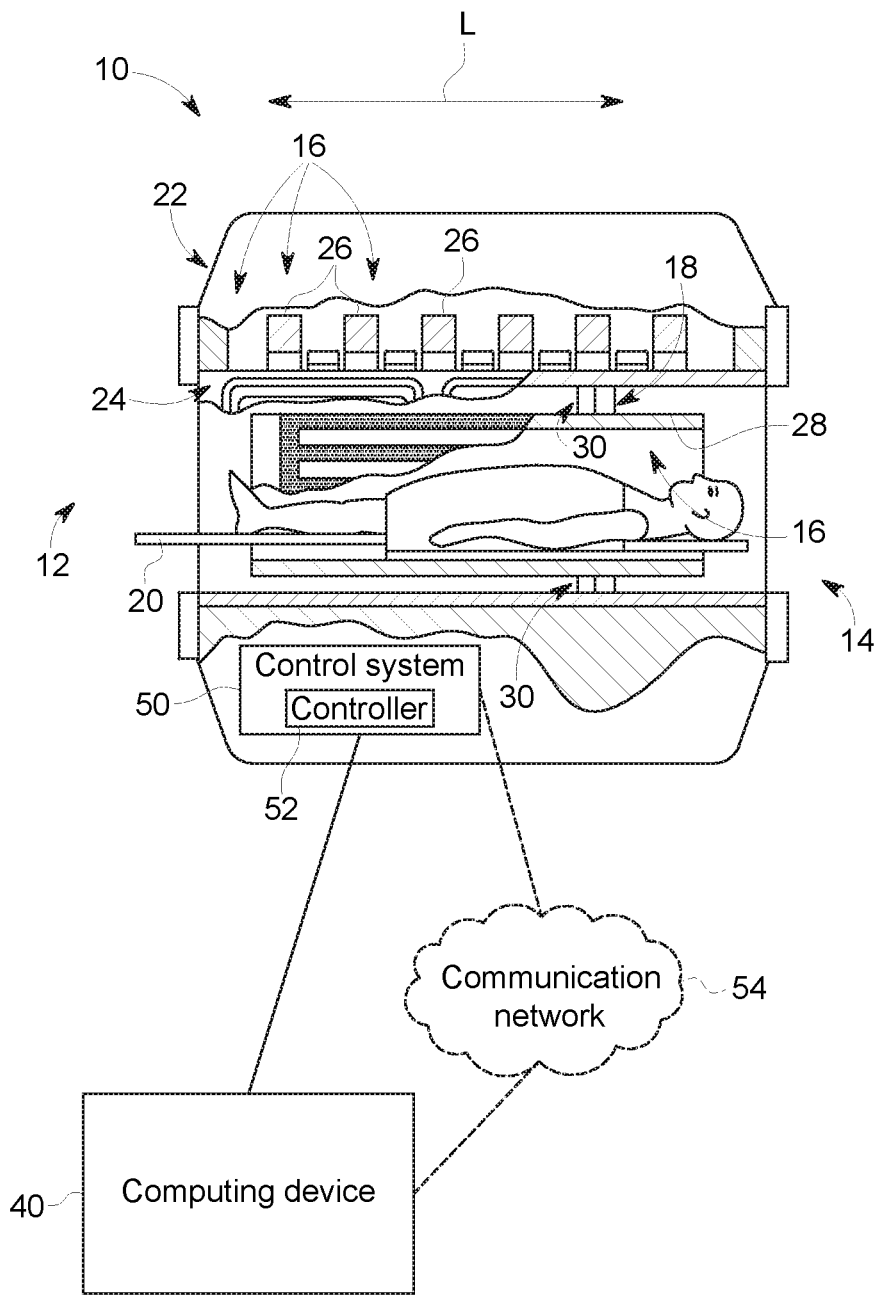
FIG. 1 is a block diagram of an embodiment of a PET-MRI scanner.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

A SiPM pixel consists of 100 to 30000 microcells and each microcell consists of a Geiger avalanche photodiodes and a quenching resistor. The fall time of a SiPM signal, τ, is approximately $R_q*C_q+C_{tot}*RL$, where $R_q$ is the resistance of a quenching resistor; $C_q$ is the capacitance of one photodiode; $C_{tot}$ is the sum of all photodiode capacitance; and RL is a load or input resistance to an amplifier. With, as an example, a $C_q$ of 90 (femtofarad) fF, an $R_q$ of 130 kOhm, RL of 50 Ohm, and a SiPM with 10,000 microcells, the total capacitance of $C_{tot}$, 90 fF*10000 microcells=900 (picofarad) pF, yields 45 nanosecond (ns) for $C_{tot}*RL$ compared to 11.7 ns for $R_q*C_q$. The effect of total capacitance $C_{tot}*RL$ is already larger than the intrinsic SiPM property of $R_q*C_q$. Each SiPM can be individually readout, but typically it involves utilizing many amplifiers for an array of SiPMs. To reduce the amount of electronics as well as its cost and power consumption, multiple SiPM devices can be combined to one timing channel that utilizes high power and high bandwidth. As an example, when 10 SiPMs are combined, the second component in the fall time, $C_{tot}*RL$, becomes 10 times larger, 10*900 pF*50 Ohm=450 ns, which reduces both the electrical current signal in the rising edge and gamma ray event count capability due to the long signal fall time. The proposed architecture reduces or minimizes the effect of $C_{tot}*M$ (M is the number of SiPMs combined) with an amplifier of low input impedance, RL, which keeps the integrity of timing signal pulse and gamma ray event count capability.

Disclosed embodiments are directed to apparatus and methods of processing analog signals generated by one or more SiPMs (e.g., photodetectors). For example, a scintillation block detector is provided that consists of an array of scintillation crystals and an array of SiPM pixels, which are optically coupled (with and without a light pipe between them). Timing signals from each SiPM in the array of SiPMs are combined at the common-anode while minimizing the effect of combined capacitance of all SiPMs on the timing signal length. The common-anode readout with a low impedance common-base or common-gate amplifier maintains the integrity of rising edge of the timing signal pulse for better timing pickoff and keeps its signal length for high count capable detector while individual cathode signals are multiplexed for energy and positional information. In one embodiment, a multichannel readout front-end application-specific integrated circuit (ASIC) interfaces with an array of SiPMs in a positron emission tomography (PET) system. The ASIC is configured to provide information on the timing, energy, and location of events in each SiPM to a processing system without having to individually or separately control the voltage of the analog anode output signal for each SiPM. In particular, analog signals from the cathode sides of an array of SiPMs (e.g., capacitive coupled to a front-end circuit) provide the energy and location of events. This enables analogs signals from the anodes sides of the array of SiPMs to be combined into a single timing signal or readout provided to a single fast amplifier (e.g., low input impedance amplifier such as a common-base or common-gate amplifier) of a time discriminating circuit. Utilizing a single combined timing signal reduces the electrical noise affecting the timing signal as each additional amplifier adds noise quadratically. Since only a single fast amplifier is utilized, a higher bandwidth can be utilized without much increase in power consumption and, thus, providing better timing capability. In addition, power consumption may be reduced utilizing the single fast amplifier resulting in less thermal cooling and less restriction in the ASIC power requirement. Further, these improvements enable a larger array of SiPMs or larger SiPMs for a block detector, while achieving a better timing performance. Increasing the detector block reduces the electronics needed in a system and, thus, reduces cost. Overall, the disclosed embodiments enable the combination of the timing signals of multiple SiPM devices while keeping the same signal integrity of a single SiPM device.

FIG. 1 depicts one example of a hybrid or combined positron emission tomography (PET)—magnetic resonance imaging (MRI) scanner 10 that can be used in conjunction with various embodiments. The scanner 10 can generally extend longitudinally along a longitudinal axis L from a proximal end 12 to the distal end 14. The scanner 10 can include MRI components 16 forming an MRI scanner portion configured to acquire MR data and/or PET imaging components 18 forming a PET image scanner portion configured to acquire PET image data, and a support structure, e.g., a bed 20 (or table), configured to translate along the longitudinal axis L from the proximal end 12 to the distal end 14 to position the bed 20 with respect to a field of view (FOV) of the MRI scanner portion and a FOV of the PET scanner portion. Although some embodiments described herein include PET-MR embodiments, it will be understood that other embodiments can include PET, PET-CT, PET-MR and/or other gamma ray detectors.

In some embodiments, the MRI components 16 can include a magnet assembly 22 and a gradient coil assembly 24, which can be implemented separately or as part of the magnet assembly 22. The magnet assembly 22 can include a polarizing main magnet 26. The MRI components 16 can include an RF coil assembly 28, which can be implemented as a radio frequency (RF) transmit coil and a phased array receive coil. The RF coil assembly 28 can be configured to transmit RF excitation pulses and to receive MR signals radiating from the subject in response to the RF excitation pulses. The gradient assembly 24 can include one or more physical gradient coils (e.g., three gradient coils having orthogonal axes) to produce magnetic field gradients to spatially encode acquired MR data output from the scanner 10 according to a k-space or raw data matrix.

The PET imaging components 18 of the scanner 10 can include a positron emission detector 30, configured to detect gamma rays from positron annihilations emitted from a subject. Detector 30 can include scintillators and photon detection electronics. The detector 30 can be of any suitable construction and have any suitable arrangement for acquiring PET data. For example, in exemplary embodiments, the detector 30 can have a ring configuration. Gamma ray incidences captured by the scintillators of the detector 30 can be transformed, by the photon detector 30, into electrical signals, which can be conditioned and processed to output digital signals that can match pairs of gamma ray detections as potential coincidence events. When two gamma rays strike detectors approximately opposite one another, it is possible, absent the interactions of randoms and scatters detections, that a positron annihilation took place somewhere along the line between the detectors. The coincidences can be sorted and integrated as PET data that can be processed and/or stored via a computing system 40.

In an exemplary embodiment, the scanner 10 can include a control system 50 having a processing device, e.g., controller 52, for controlling an operation of the scanner 10. The controller 52 of the control system 50 can be programmed and/or configured to control an operation of the MRI components 16, PET components 18, and/or bed 20. While the control system 50 is depicted as being included in the scanner 10, those skilled in the art will recognize that the control system 50, or portions thereof, can be implemented separately and apart from the scanner 10 and can be communicatively coupled to the scanner 10. The control system 50 can be in communication with a computing device 40 such that the scanner 10 can be programmed and/or controlled, via a computing system 40 communicatively coupled to the control system 50 to transmit data and/or commands to the controller 52 of the control system 50 to control an operation of the scanner 10. In some embodiments, the computing device 40 can be in communication with the control system 50 via a communications network 54. In some embodiments, the computing device 40 includes an ASIC, such as ASIC 120 described below with respect to FIG. 2.

In exemplary embodiments, the computing system 40 can configure and/or program the controller 52 of the control system 50 to control the MRI components 16, PET components 18, and/or the bed 20 to perform a scan sequence in response to instructions, commands, and/or requests transmitted to the control system 50 by the computing device 40. As one example, the controller 52 of the control system 50 can be programmed to acquire a sequence of PET images by passing the bed, upon which the subject is supported, through the field of view of the PET scanner portion of the scanner 10. As another example, the controller 52 of the control system can be programmed and/or configured (e.g., via the computing device 40) to generate RF and gradient pulses of a scan sequence for acquisition of MR images.

Gradient pulses can be produced during the MR data acquisition by controlling one or more physical gradient coils in a gradient coil assembly 24 to produce magnetic field gradients to spatially encode acquired MR data output from the scanner 10. MR signals resulting from the excitation pulses, emitted by excited nuclei in a subject, can be sensed by the RF coil assembly 28, and can be provided to the computing system for processing. In some embodiments, PET data and MR data can be concurrently acquired by the scanner 10.

Figure 2:
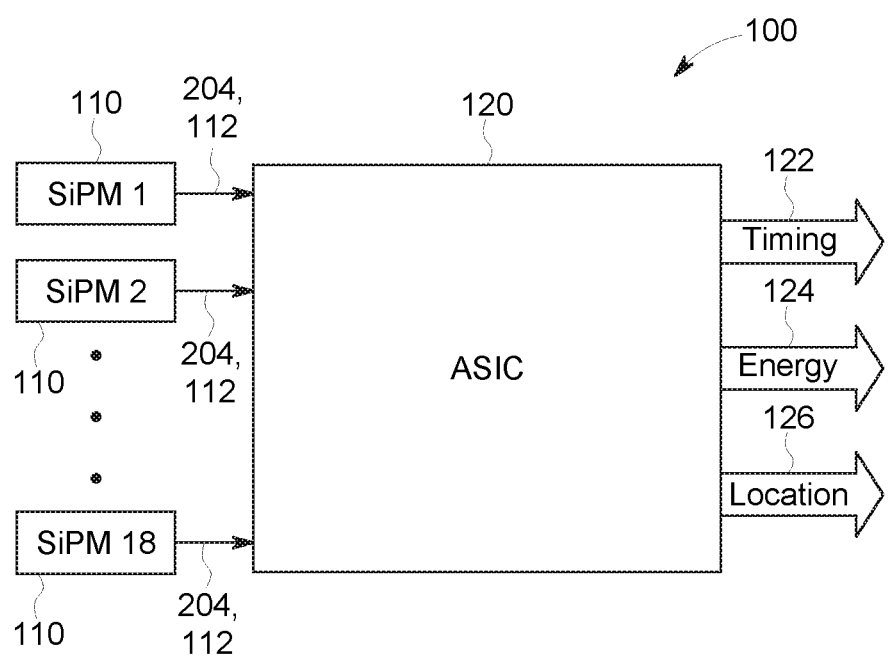
FIG. 2 is a block diagram of an embodiment of a PET data acquisition system.

FIG. 2 is a block diagram of one example of a PET data acquisition system 100, according to one embodiment. The system 100 may, for example, be included in the scanner 10. The system 100 includes a plurality of SiPMs 110 (e.g., photodetectors), and an ASIC 120. Each SiPM 110 includes an array of microcells that each includes an avalanche photodiode and a quenching resistor. Each SiPM 110 has an analog anode output 204 (e.g., received by the time discriminating circuit 420) and an analog cathode output 112 (e.g., received by the front-end circuit 410) in electrical communication with the ASIC 120. The outputs 204, 112 are different from one another. When a 511 keV gamma ray interacts with a scintillator, light is generated. This scintillated light is detected by at least one of the SiPMs 110 and rapidly amplified. The anode output 204 and the cathode output 112 can be used as inputs to the ASIC 120, such as described below. The ASIC 120 provides, as outputs, one or more timing signals 122, energy signals 124 and/or position signals 126 each representing information obtained by the SiPMs 110 from, for example, a PET scanner (not shown) after processing by the ASIC 120. In an exemplary embodiment, the system 100 can include eighteen (18) SiPMs 110, although it will be understood that in other embodiments different quantities of SiPMs 110 can be used.

Figure 3:
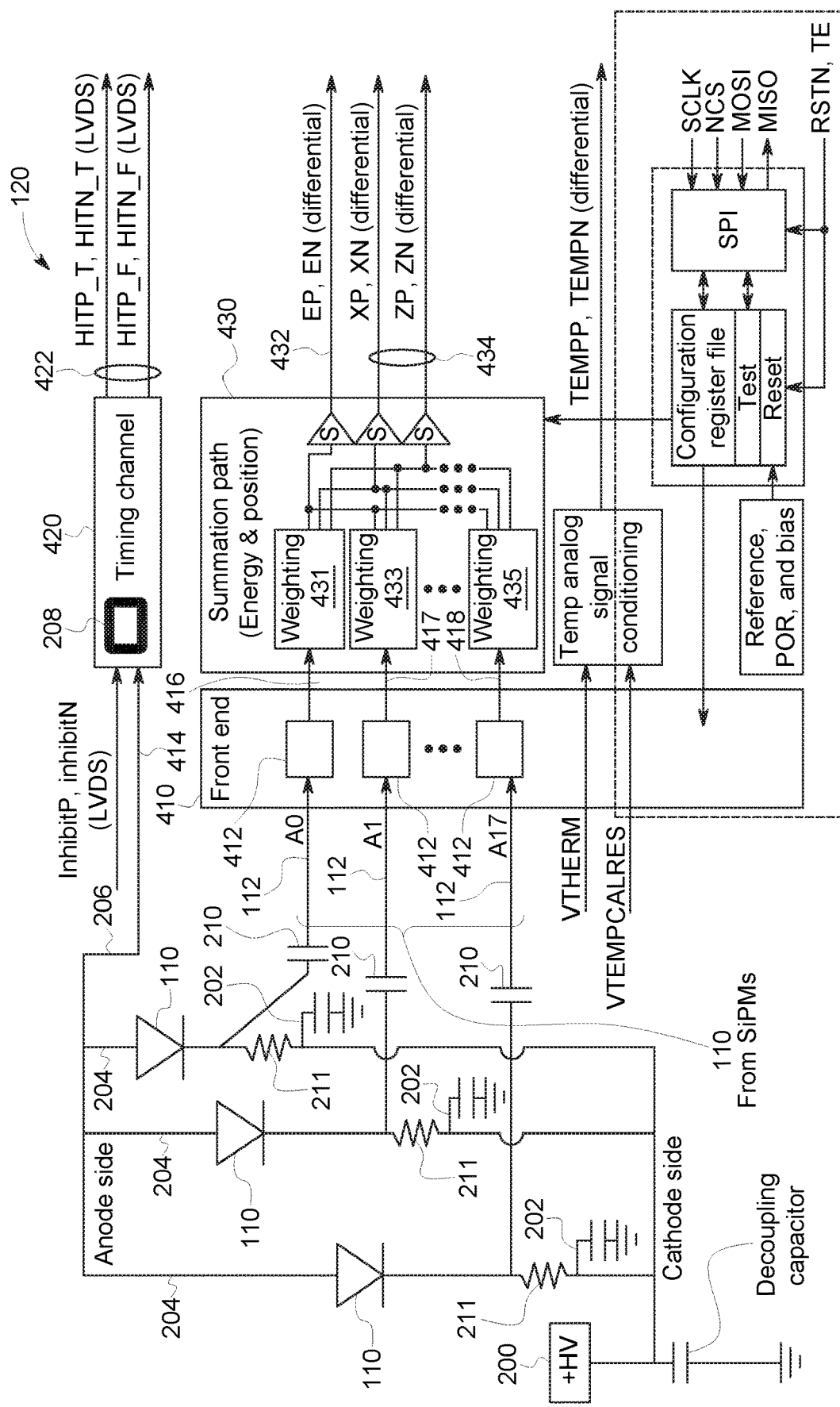
FIG. 3 is a block diagram of an embodiment of an ASIC.

FIG. 3 is a block diagram of one example of the ASIC 120 of FIG. 2, according to one embodiment. The ASIC 120 includes a front-end circuit 410, a time discriminating circuit 420, and an energy discriminating circuit 430. The front-end circuit 410 and the time discriminating circuit 420 are not operably coupled (i.e., not coupled via a channel). A common high voltage source 200 provides a high voltage (e.g., bias voltage) to the SiPMs 110 that include decoupling capacitors 202 on the cathode side for a fast charge supply. The high voltage supplied may be positive or negative, depending on cathode or anode sides. As depicted in FIG. 3, a positive high voltage is applied on the cathode sides. In certain embodiments (see FIG. 11), a negative high voltage is applied on the anode sides, while the anodes sides are capacitive coupled (i.e., AC coupled) to the front-end circuitry 410, and the cathode sides are conductive coupled (i.e., DC coupled) to the time discriminating circuitry 420. As depicted in FIG. 3, the anode sides of the SiPM devices 110 are conductive coupled to the time discriminating circuitry 420. Analog anode outputs 204 are combined into a single timing signal 206 (i.e., summation of signals) from the SiPMs 110 and provided to time discriminating circuit 420 for generating timing information at outputs 422. The time discriminating circuit 420 can process the combined signal 206 corresponding to the outputs 204 of the SiPMs 110 to generate a timing HIT signal (e.g., representing an indication that radiation has been detected by the SiPMs 110) at outputs 422. The time discriminating circuit 420 includes a fast (e.g., >200 megahertz (MHz)), low input impedance amplifier 208, such as a common-base or common-gate amplifier to amplify from the input signal 206 and provide a comparator to generate a timing HIT signal. The input impedance of the timing amplifier 208 is 1 Ohm or less. The fall time of the timing signal would be affected by a sum of all SiPM capacitance. However, the effect of the capacitance sum is minimized due to the small input impedance, RL, of the timing amplifier 208. As an example from the background section, $RL*C_{tot}*(10\ SiPMs)=1\ Ohm*900\ pF*10=9\ ns$, which is much smaller than in case of 50 Ohm with RL. Also, due to the low breakdown voltage variability and SiPM sorting for breakdown voltages there is no need for individual or separate anode voltage control for each SiPM 110 via a multichannel digital-to-analog converter.

Figure 5:
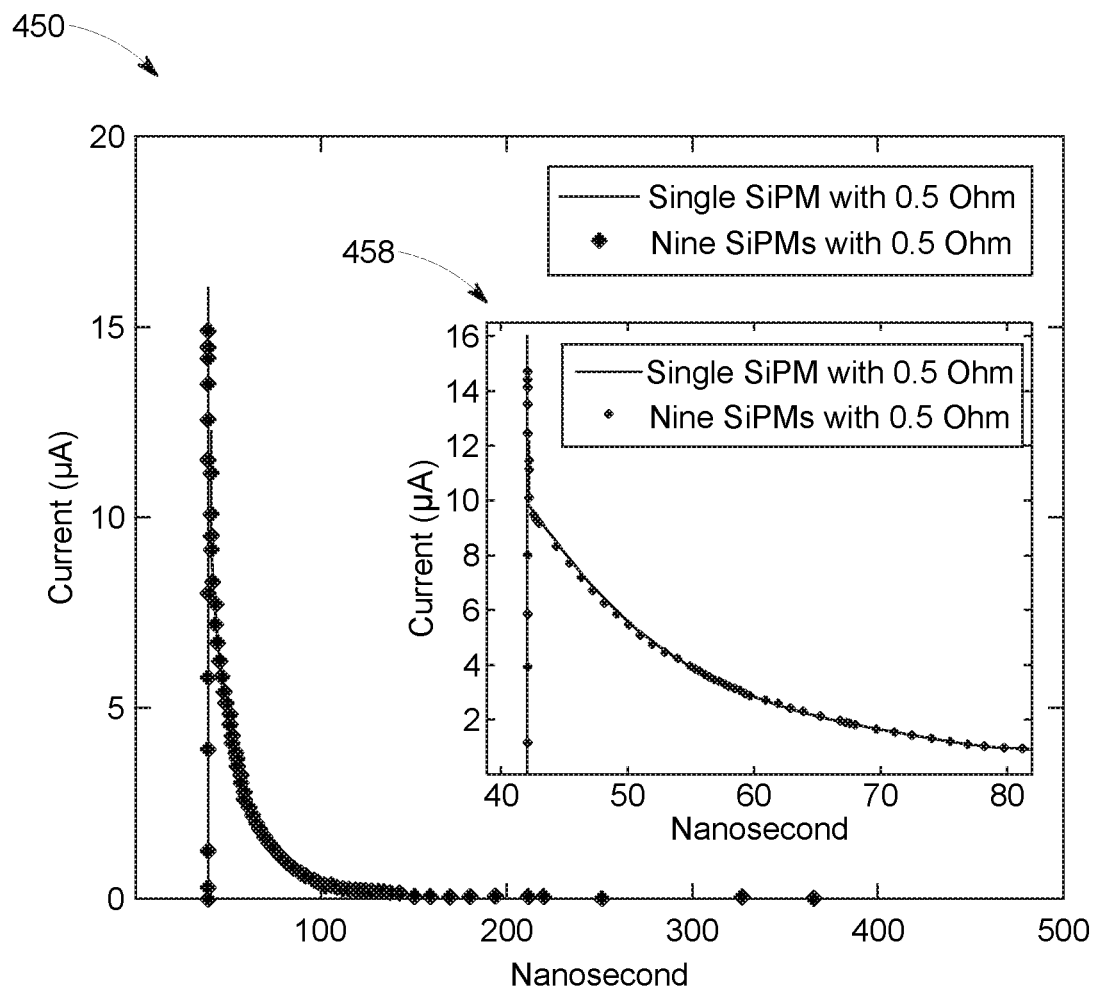
FIG. 5 is a plot of a single photon pulse for a single SiPM device versus nine SiPM devices with 0.5 Ohm input impedance utilizing the SPICE model of FIG. 4.

The absence of anode voltage control (e.g., via a DAC) enables each cathode side of the SiPMs 110 to include a resistor 211 that is configured to pick up an energy signal from the SiPM 110 (resulting in a voltage drop across the resistor) when an individual pixel or microcell are hit by radiation. Due to the high voltage applied at the cathode, the voltage drop across the resistors was AC coupled to generate the analog cathode outputs 112 of the SiPM devices 110 (e.g., capacitive coupled as indicated by reference numeral 210), which subsequently fed to the ASIC front-end 410, such as shown in FIG. 5 and described below. In certain embodiments, when a negative high voltage is applied on the anode sides of the SiPM devices 110 the anodes sides are capacitive coupled (i.e., AC coupled) to the front-end circuitry 410, and the cathode sides are conductive coupled (i.e., DC coupled) to the time discriminating circuitry 420. The front-end circuit 410 can function as a current buffer, and can include one or more amplifiers 412 (e.g., one for every one or two or more SIPMs 110 depending on the capacitance of SiPMs) that are lower power (e.g., <3 mW/operational amplifier) and low bandwidth (e.g., 18 MHz or less), which preserve the energy information of the input signals. In certain embodiments, the front-end circuit 410 may include 18 amplifiers 412 for 18 SiPMs 110. The utilization of one combined anode side timing readout 420 (instead of multiple fast amplifiers) reduces the power requirement for energy signals in the front-end 410 of the ASIC 120.

The amplified signals from each of the amplifiers 412 can be output by the front-end circuit 410 on lines 416, 417 or 418, each corresponding to a respective SiPM 110. The amplified signals can be output from the front-end circuit 410 to the energy discriminating circuit 430, which can be configured to generated energy and position information at outputs 432 and 434, respectively. For example, the position information may include two-dimensional (e.g., x and z axis) position information provided on separate outputs. In certain embodiments, 18 SiPMs 110 may be connected to the front-end circuit 410.

In exemplary embodiments, the energy discriminating circuit 430 can apply weightings 431, 433, 435 to the signals received on lines 416, 417, and 418, respectively. The weighted signals can each have three components: a first component (e.g., an energy output), a second component (e.g., a row output), and a third component (e.g., a column output). Each of the first components can be summed and output on line 432 as a summed energy output. Each of the second components can be summed and each of the third components can be summed. The summed second and third components can be output on line 434 as summed row and column outputs.

The energy circuit 430 can sum a scaled version of the front-end outputs 416, 417, and/or 418 with programmable weights (e.g., weighting 431, 433, 435) to generate energy and position signals at outputs 432 and 434, respectively. A controller (not shown) can interface with an external FPGA (not shown) to configure and set the weights.

Figure 4:
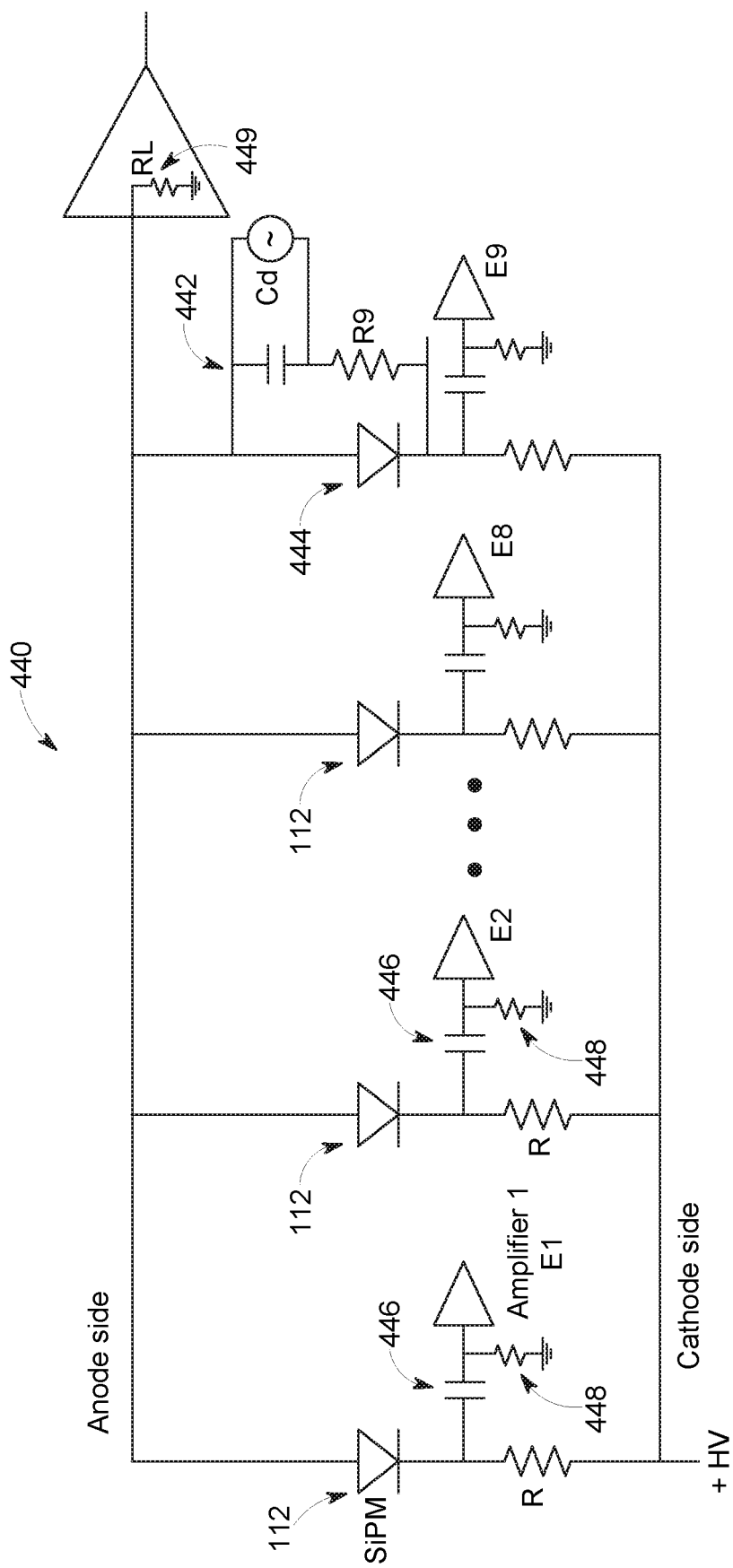
FIG. 4 is a schematic diagram of an embodiment of a simulation program with integrated circuit emphasis (SPICE) model of a plurality of SiPM devices where a single microcell of one SiPM device is firing (with positive high voltage applied)

FIG. 4 is a schematic diagram of an embodiment of a simulation program with integrated circuit emphasis (SPICE) model 440 simulating a plurality of SiPM devices 112 where a single microcell 442 of one SiPM device 444 is firing (i.e., responding to radiation hit and generating a single photon pulse). The model 440 illustrates individual readout of the cathode side of the SiPM devices 112 with a capacitor 446 (e.g., via AC coupling) and a resistor 448 going to ground. The model 440 includes all signals (e.g., analog signals) being combined (e.g., into a single signal) in the anode side. In addition, the model 440 includes the simulation of the input impedance of an anode side receiver amplifier, RL, 449 with a resistor having a resistance of 0.1, 1, 10, and 30 Ohm, respectively. Each SiPM device 112 in the model 440 includes a total capacitance, $C_{tot}$, of 738 picofarad (pF).

Figure 6:
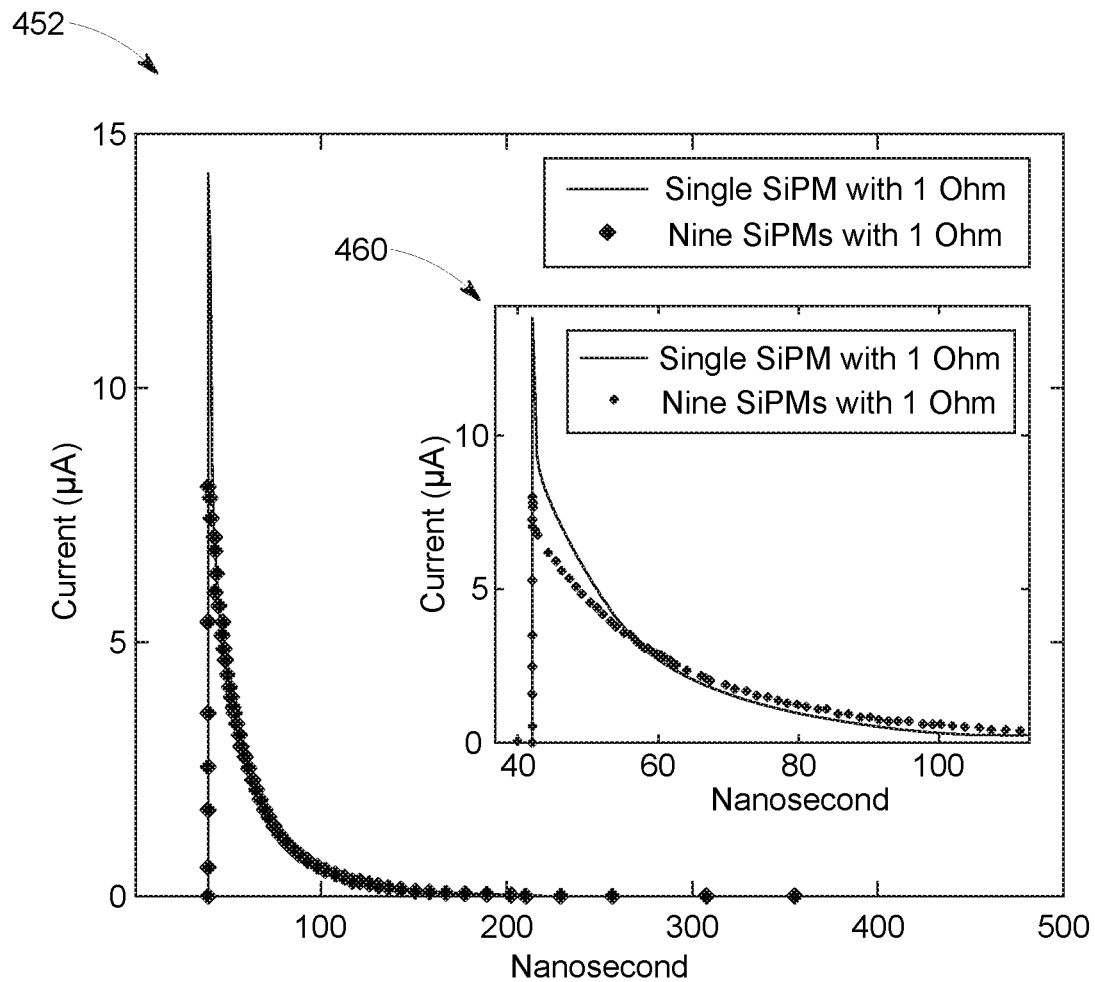
FIG. 6 is a plot of a single photon pulse for a single SiPM device versus nine SiPM devices with 1 Ohm input impedance utilizing the SPICE model of FIG. 4.
Figure 7:
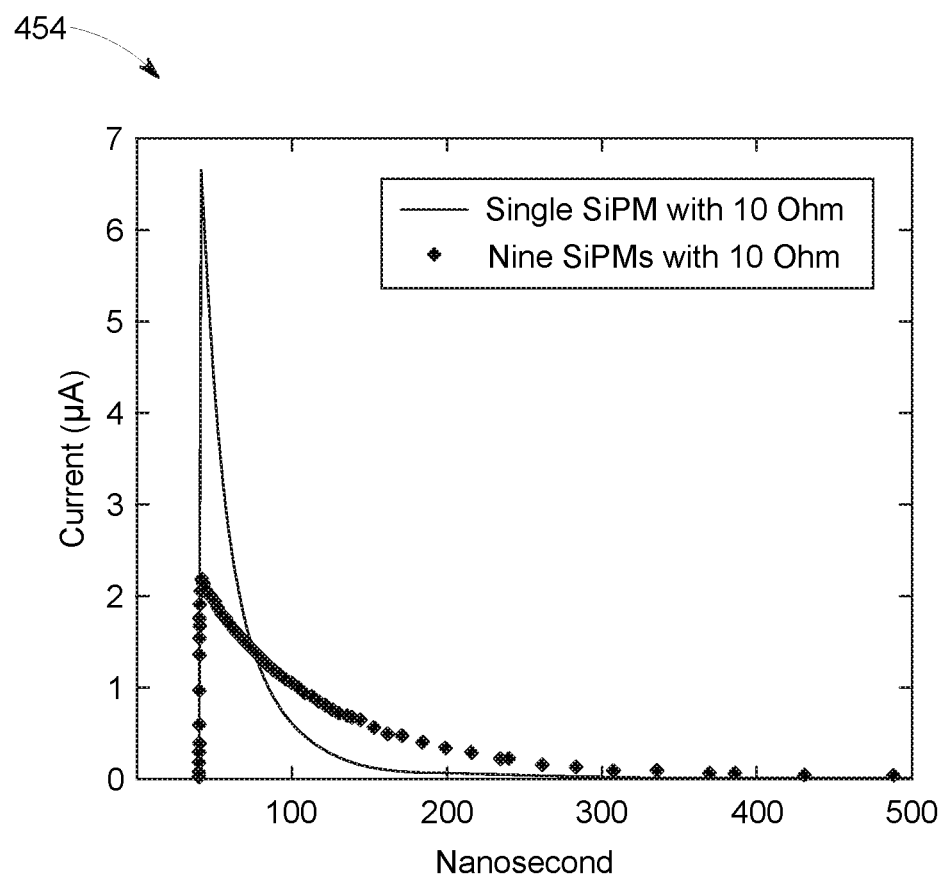
FIG. 7 is a plot of a single photon pulse for a single SiPM device versus nine SiPM devices with 10 Ohm input impedance utilizing the SPICE model of FIG. 4.
Figure 8:
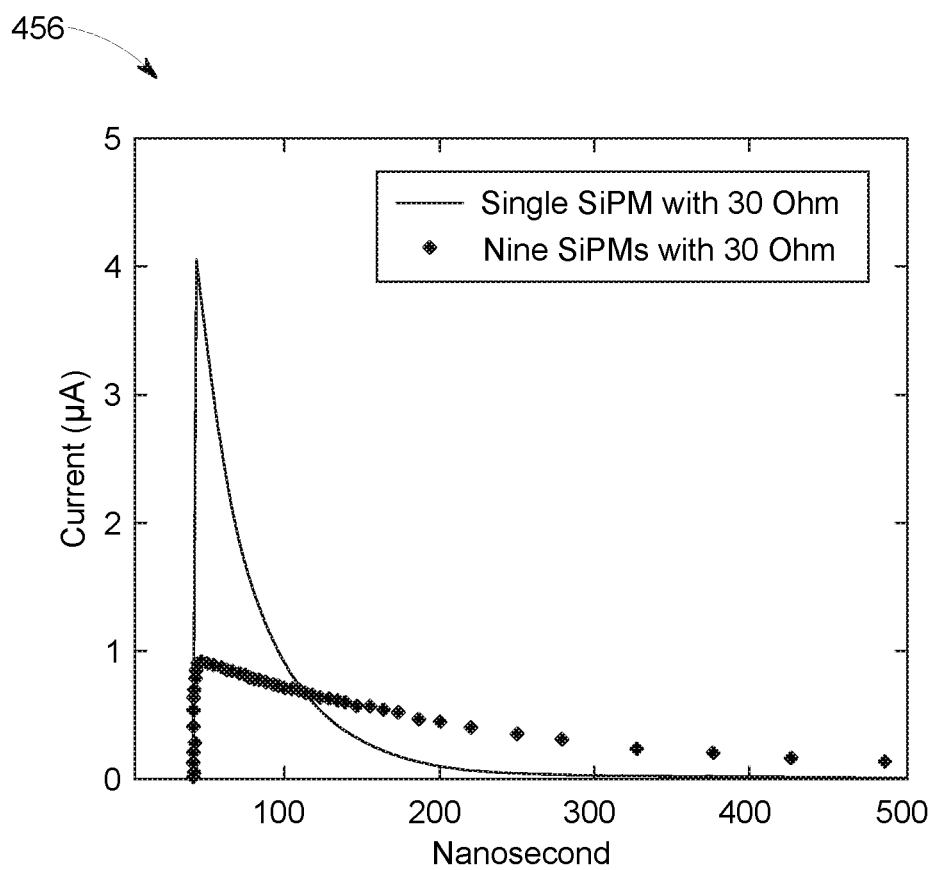
FIG. 8 is a plot of a single photon pulse for a single SiPM device versus nine SiPM devices with 30 Ohm input impedance utilizing the SPICE model of FIG. 4.

FIGS. 5-8 are plots 450, 452, 454, 456 of a single photon pulse for a single SiPM device versus nine total SiPM devices (i.e., combined) with 0.5, 1, 10, and 30 Ohm input impedance, respectively, utilizing the SPICE model 440 of FIG. 4. FIGS. 5 and 6 include insets 458, 460 of the plots 450, 452 along shorter time axes. As illustrated in FIG. 5, there is little difference between the peak currents and fall times of the single photon pulse for the single SiPM device versus nine SiPM devices with 0.5 Ohm input impedance. For example, at 0.5 Ohm resistance, the fall times for a single SiPM device versus the nine total SiPM devices is 12.1 nanoseconds (ns) and 15.3 ns, respectively. As the input impedances increase the fall times get longer and the peak currents (which are critical for good timing resolution) get reduced as illustrated in FIGS. 6-8.

Figure 9:
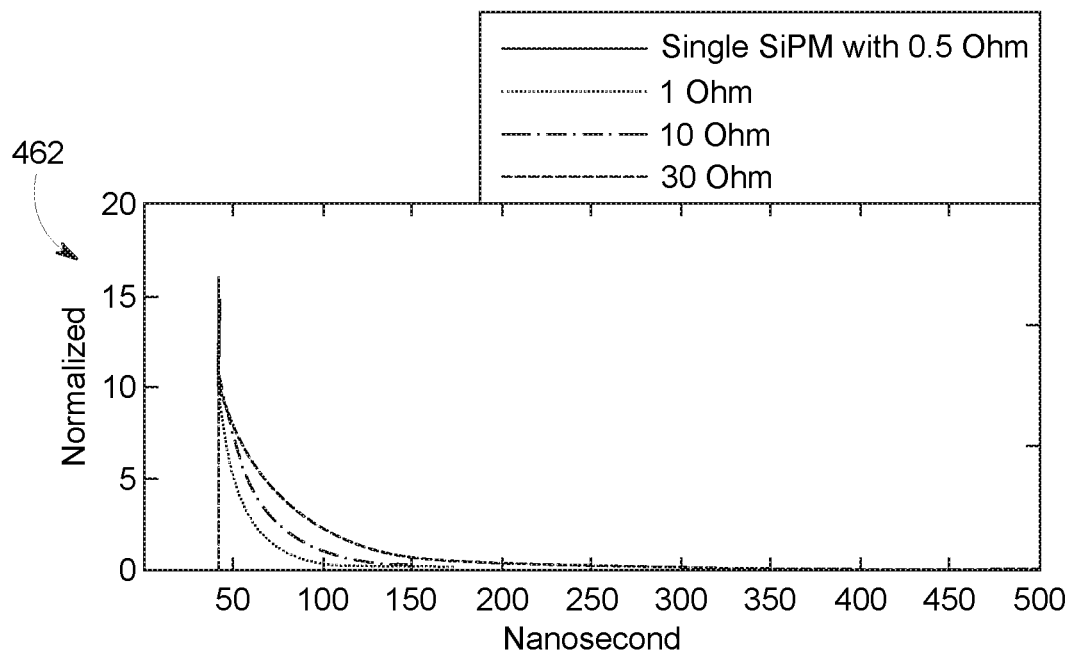
FIG. 9 is a plot of the single photon pulses for the single SiPM device for the different input impedances in FIGS. 5-8 with peak height normalized.
Figure 10:
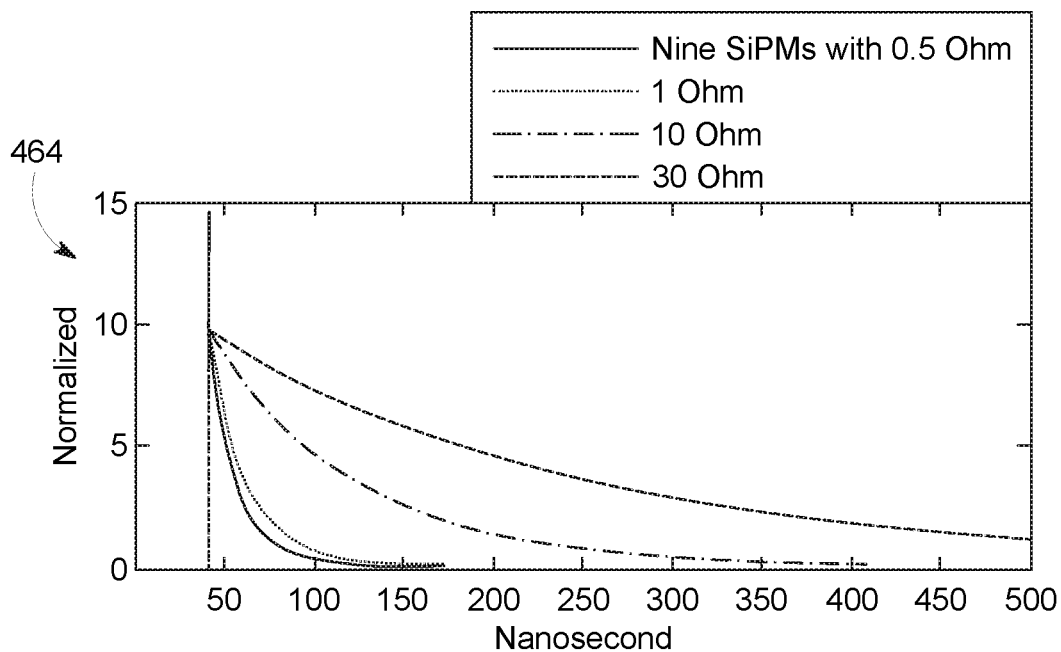
FIG. 10 is a plot of the single photon pulses for the nine total SiPM devices for the different input impedances in FIGS. 5-8 with peak height normalized.

FIGS. 9 and 10 are plots 462, 464 of the single photon pulses for the single SiPM device and the nine total SiPM devices, respectively, for the different input impedances in FIGS. 5-8 with peak height normalized. As illustrated, in FIG. 9, the different input impedances has a minor effect on the fall time for the single SiPM device. However, as illustrated, in FIG. 10, as the input impedances increase the fall time for the tail pulse for the combined nine SiPM devices increases significantly. For optimal timing resolution and obtaining a high count rate PET detector, it is important to keep the pulse short (e.g., with a maximal peak and short fall time). Thus, minimizing the input impedance (e.g., by utilizing a single low input impedance or transimpedance amplifier or common-base or common-gate amplifier in the timing circuit as opposed to multiple fast amplifiers in the front-end circuit) enables one to combine the timing signals from the multiple SiPM devices into a single signal from the anode outputs, while keeping the same signal integrity of a single SiPM device. For example, a low impedance amplifier of an input impedance of 1 Ohm or a common-base or common-gate amplifier with an input impedance of less than 1 Ohm (e.g., 0.5 Ohm) can be utilized.

Figure 11:
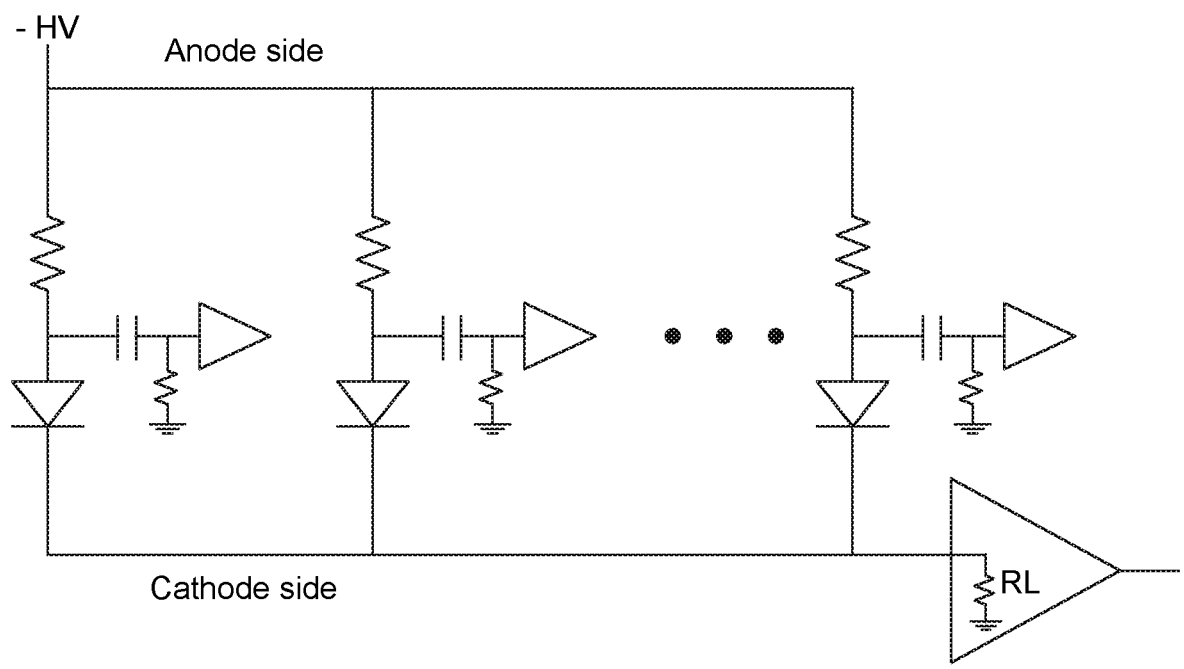
FIG. 11 is a schematic diagram of an embodiment of a simulation program with integrated circuit emphasis (SPICE) model of a plurality of SiPM devices where a single microcell of one SiPM device is firing (with negative high voltage applied).

FIG. 4, above, illustrates an exemplary schematic for utilizing anode summing for the timing signal. Since the operation of SiPM avalanche photodiode requires a reverse bias, when a negative high voltage is applied to anodes, the timing signal summing can be achieved on the cathode side as shown in FIG. 11 to achieve the same benefits in power and signal integrity. As illustrated in FIG. 11, the decoupling capacitors are located on the anode sides of the SiPMs, the anodes sides of the SiPMs are capacitive coupled to the front-end circuitry, and the cathode sides are conductive coupled (i.e., DC coupled) to the time discriminating circuitry.

Technical effects of the disclosed embodiments include providing apparatus and methods of processing analog signals generated by one or more SiPMs that minimize input impedance (e.g., the external load in the electronics coupled to the SiPM devices), while combining the timing signals from multiple SiPM devices into a single signal from the anode inputs and keeping the same signal integrity of a single SiPM device. Utilizing a single combined timing signal reduces the electrical noise affecting the timing signal. Since only a single fast amplifier is utilized, a higher bandwidth amplifier can be utilized without much increase in power consumption and, thus, providing better timing capability. In addition, power consumption may be reduced utilizing the single fast amplifier resulting in less thermal cooling and less restriction in the ASIC power requirement. Further, these improvements enable a larger array of SiPMs or larger SiPMs for a block detector, while achieving a better timing performance. Increasing the detector block reduces the electronics needed in a system and, thus, reduces cost.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A multichannel application specific integrated circuit (ASIC) for interfacing with an array of photodetectors in a positron emission tomography (PET) imaging system, the ASIC comprising:
   a front-end circuit configured to be coupled to the array of photodetectors and to receive a plurality of discrete analog signals therefrom, wherein the front-end circuit is coupled to a respective cathode of each photodetector in the array of photodetectors;
   a time discriminating circuit comprising a low input impedance amplifier that is configured both to be coupled to the array of photodetectors and to receive a signal summing a plurality of analog signals from the array of photodetectors and the time discriminating circuit is configured to generate a hit signal for timing pickoff based on the signal; and
   an energy circuit operably coupled to the front-end circuit and configured to generate a summed energy output signal and a summed positional output signal based on each of the analog signals, the summed energy output signal representing an energy level of the detected radiation in the array of photodetectors, and the summed positional output signal representing a location of the detected radiation in the array of photodetectors.

2. The ASIC of claim 1, wherein the front-end circuit for energy and positional signals is not coupled to the time discriminating circuit.

3. The ASIC of claim 1, wherein the low input impedance amplifier has a bandwidth greater than 200 MHz.

4. The ASIC of claim 1, wherein the front-end circuit is configured to be capacitive coupled to each photodetector in the array of photodetectors.

5. The ASIC of claim 1, wherein the time discriminating circuit is conductive coupled to each photodetector in the array of photodetectors.

6. The ASIC of claim 5, wherein the timing discriminating circuit is conductive coupled to an anode side of each photodetector in the array of photodetectors.

7. The ASIC of claim 1, wherein the low input impedance amplifier comprises a common-base amplifier or common-gate amplifier.

8. The ASIC of claim 1, wherein positional signals are summed with configurable weights depending on a respective location of each photodetector in the array of photodetectors.

9. The ASIC of claim 1, wherein the low input impedance amplifier has an input impedance of 1 Ohm or less.

10. The ASIC of claim 1, wherein the front-end circuit comprises at least one low power amplifier of less than 3 mW power.

11. The ASIC of claim 1, wherein the array of photodetectors comprises an array of Geiger-mode avalanche photodiodes.

12. A method of interfacing with an array of photodetectors in a positron emission tomography (PET) imaging system, comprising:
   receiving analog signals from each photodetector in the array of photodetectors using a front-end circuit, wherein the front-end circuit is coupled to a respective cathode of each photodetector in the array of photodetectors;
   generating a hit signal for timing pickoff based on a signal summing the analog signals from the array of photodetectors using a time discriminating unit comprising a low input impedance amplifier that receives the signal summing the analog signals;
   generating a summed energy output signal based on each of the analog signals using an energy circuit operably coupled to the front-end circuit, the summed energy output signal representing an energy level of the detected radiation in the array of photodetectors; and
   generating a summed positional output signal based on each of the analog signals using the energy circuit, the positional output signal representing a location of the detected radiation in the array of photodetectors.

13. The method of claim 12, wherein the front-end circuit for energy and positional signals is not coupled to the time discriminating circuit.

14. The method of claim 12, wherein the low input impedance amplifier has a bandwidth greater than 200 MHz.

15. The method of claim 12, wherein the front-end circuit is capacitive coupled to each photodetector in the array of photodetectors.

16. The method of claim 12, wherein the time discriminating circuit is conductive coupled to an anode side of each photodetector in the array of photodetectors.

17. The method of claim 12, wherein the low input impedance amplifier has an input impedance of 1 Ohm or less.

18. A multichannel application specific integrated circuit (ASIC) for interfacing with an array of photodetectors in a positron emission tomography (PET) imaging system, the ASIC comprising:
   a front-end circuit configured to be capacitive coupled to each photodetector of the array of photodetectors and to receive analog signals therefrom, wherein the front-end circuit is coupled to a respective cathode of each photodetector in the array of photodetectors;

a time discriminating circuit comprising a low input impedance amplifier configured both to be conductively coupled to each photodetector of the array of photodetectors and to receive a signal summing the analog signals from the array of photodetectors and the time discriminating circuit is configured to generate a hit signal for timing pickoff based on the signal, wherein the low input impedance amplifier has an input impedance of 1 Ohm or less; and an energy circuit operably coupled to the front-end circuit and configured to generate a summed energy output signal based on each of the analog signals and summed positional output signal based on each of the analog signals, the summed energy output signal representing an energy level of the detected radiation in the array of photodetectors, and the summed positional output signal representing a location of the detected radiation in the array of photodetectors.

* * * * *